(12) United States Patent
Marnay

(10) Patent No.: US 11,076,894 B2
(45) Date of Patent: Aug. 3, 2021

(54) SYSTEM FOR INSERTING AND REMOVING A LOCATOR-PIN IN A BONE

(71) Applicant: STYLITECH, Montpellier (FR)

(72) Inventor: Thierry Marnay, Montpellier (FR)

(73) Assignee: STYLITECH, Montpellier (FR)

( * ) Notice: Subject to any disclaimer, the term of this patent is extended or adjusted under 35 U.S.C. 154(b) by 0 days.

(21) Appl. No.: 15/631,081

(22) Filed: Jun. 23, 2017

(65) Prior Publication Data
US 2018/0368892 A1    Dec. 27, 2018

(51) Int. Cl.
| | | |
|---|---|---|
| *A61B 17/70* | (2006.01) | |
| *A61B 17/17* | (2006.01) | |
| *A61B 17/88* | (2006.01) | |
| *A61B 17/84* | (2006.01) | |

(52) U.S. Cl.
CPC ...... *A61B 17/7079* (2013.01); *A61B 17/1757* (2013.01); *A61B 17/7082* (2013.01); *A61B 17/846* (2013.01); *A61B 17/8897* (2013.01); *A61B 17/7032* (2013.01)

(58) Field of Classification Search
CPC .................................................. A61B 17/7079
USPC ....................................... 606/103, 86 A, 104
See application file for complete search history.

(56) References Cited

U.S. PATENT DOCUMENTS

| | | | | |
|---|---|---|---|---|
| 3,719,186 | A * | 3/1973 | Merig, Jr. .......... | A61B 17/1739 606/80 |
| 5,196,015 | A | 3/1993 | Neubardt | |
| 5,456,267 | A * | 10/1995 | Stark .................... | A61B 10/025 128/898 |
| 5,954,671 | A * | 9/1999 | O'Neill .............. | A61B 17/1637 600/567 |
| 6,719,758 | B2 * | 4/2004 | Beger ................ | A61B 17/1697 606/104 |
| 2007/0270896 | A1 | 11/2007 | Perez-Cruet | |
| 2007/0276402 | A1 * | 11/2007 | Frankel .............. | A61B 17/1655 606/96 |
| 2010/0168751 | A1 | 7/2010 | Anderson | |
| 2013/0012999 | A1 * | 1/2013 | Petit ................... | A61B 17/7076 606/279 |

* cited by examiner

*Primary Examiner* — Eduardo C Robert
*Assistant Examiner* — Tara Rose E Carter
(74) *Attorney, Agent, or Firm* — Arrigo, Lee, Guttman & Mouta-Bellum LLP

(57) ABSTRACT

A locator-pin for positioning a pedicle screw in a bone, comprising a pin body, a distal portion comprising a trocar tip shaped to penetrate a bone by pressing and/or percussing and a proximal portion equipped with a first fixing member to fix, during use, to an insertion pin-carrier and a second fixing member to fix, during use, to a removal pin-carrier, the two fixing members being different, wherein the first fixing member is able to transmit at least an axial push parallel to an axis of a locator-pin, and the second fixing member is able to transmit at least an axial draw parallel to the axis of the locator-pin and at least one sense of rotation around the axis of the locator-pin. Systems comprising the locator-pin and methods of recovering a positioned locator-pin.

8 Claims, 3 Drawing Sheets

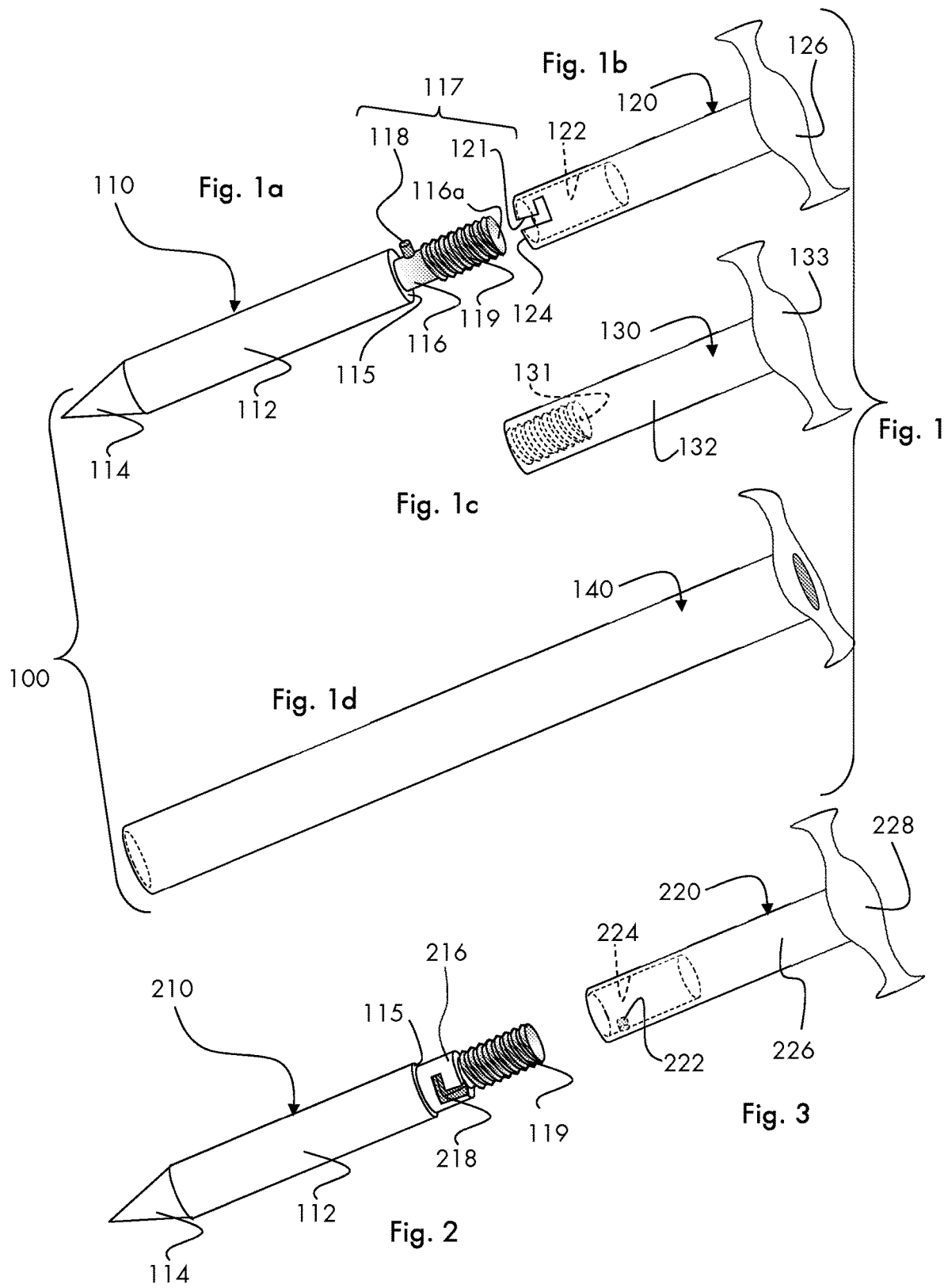

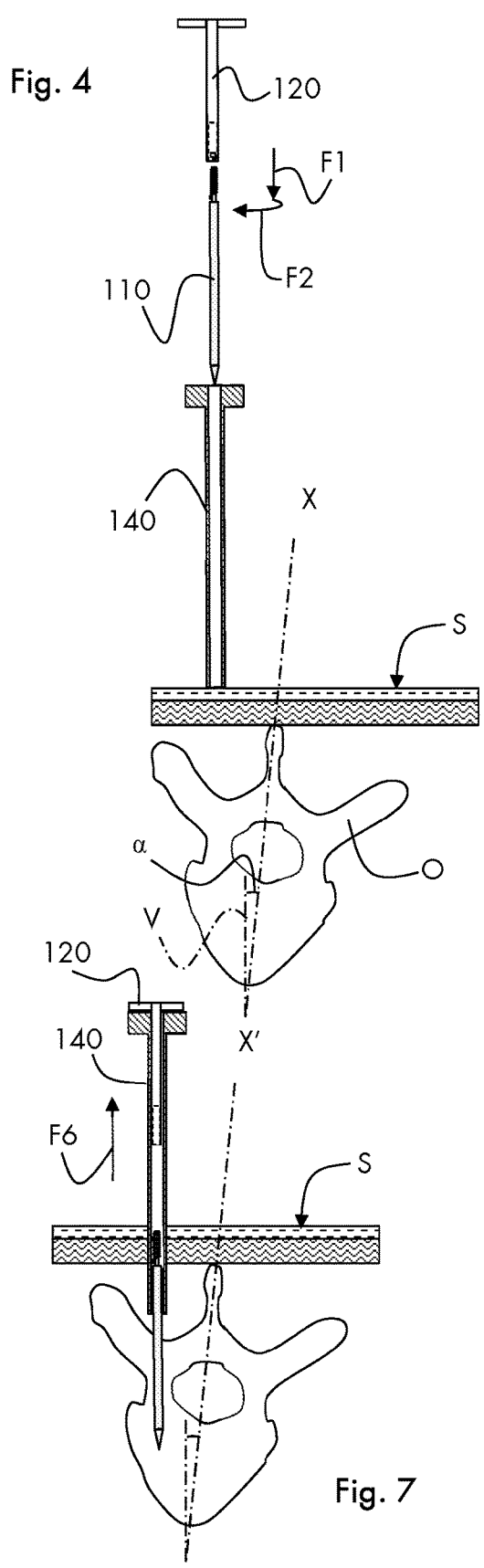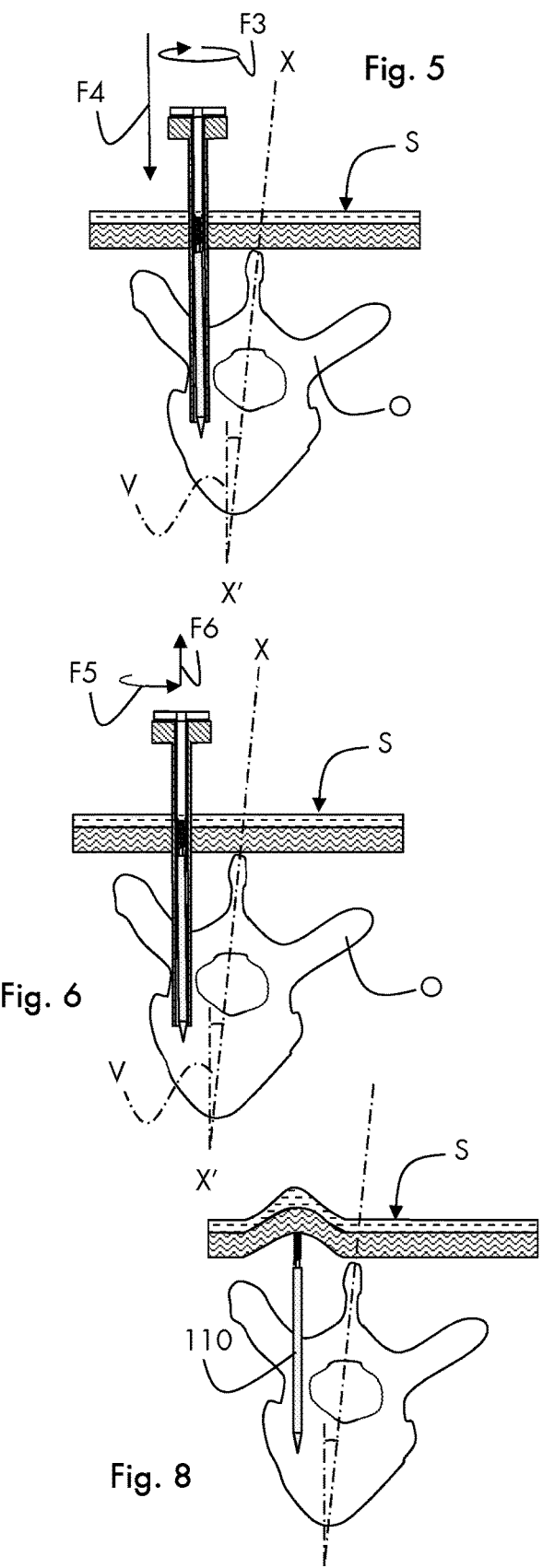

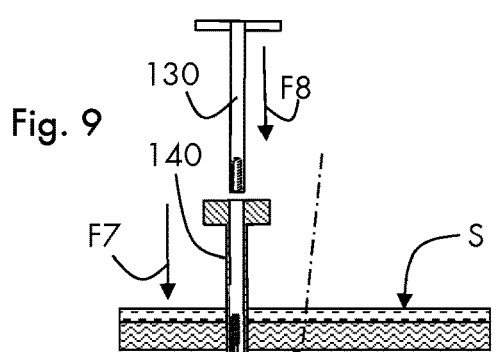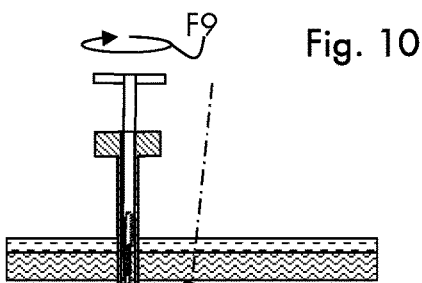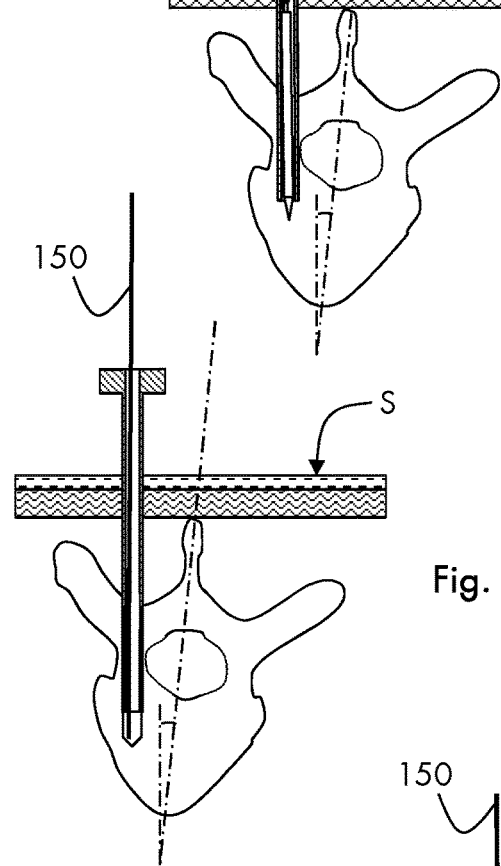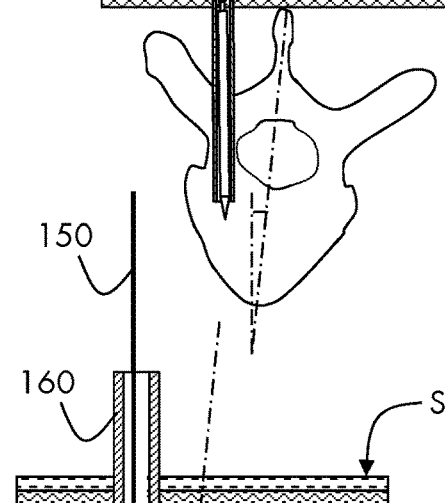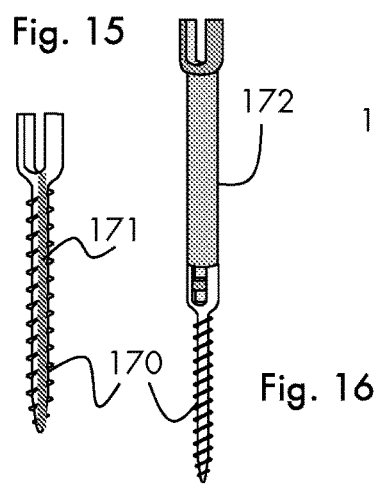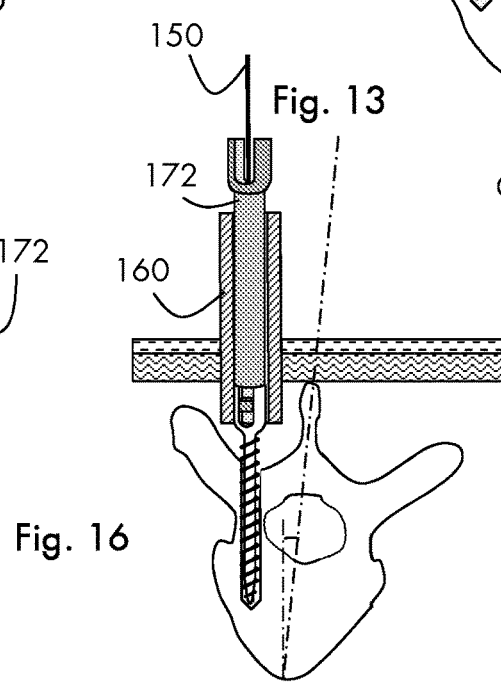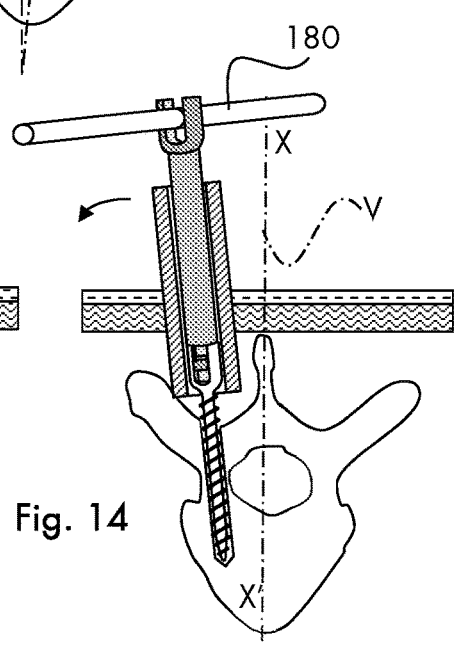

SYSTEM FOR INSERTING AND REMOVING A LOCATOR-PIN IN A BONE

This invention relates to a system for inserting and removing a locator-pin in a bone, to a locator-pin, to an insertion pin-carrier and to a removal pin-carrier.

More particularly, this invention concerns a system used for spinal surgery, in particular for installing screw-type implants for example, in order to stabilize tumor fractures, immobilize the spine in the case of arthrodesis (intervertebral grafting in order to fuse two or more vertebrae together) in degenerative diseases, and to correct deformations of the spinal column (scoliosis and kyphosis).

Since the sixties, spinal surgery has seen the development of successful osteosynthesis allowing the fixing of fractures, the immobilization of arthrodesis and above all the correction of deformations (scoliosis and kyphosis). After the use of hooks, the use of pedicle screws has become universally widespread.

Pedicle screws are inserted into the vertebrae in very specific places, the pedicles, to allow deformations to be corrected without risking damage to the spinal column or its contents, the spinal cord. For this, precise mapping is required before insertion.

Although anatomical mapping has long been studied to make this installation repetitively reliable, the fact remains that the conditions for installing these pedicle screws into the vertebrae can be delicate, particularly in deformations of the spinal column associated with a rotational impairment. Lastly, in the thoracic region of the spine, the "pedicle target" combines all aspects of difficulty: the most delicate or even impossible anatomical landmarks in the case of rotation of vertebral bodies, small pedicles and major risk of spinal cord injury in the event of cortical breach or following the wrong path.

Numerous assistance tools have been developed in order to optimize the safety and efficiency of pedicle screws, but they are insufficient.

Thus, conventional surgery to straighten the spinal column is conducted entirely in one specific operating room, equipped with an imaging system, usually an image intensifier (fluoroscopy).

The surgeon first opens up the patient and records his anatomical landmarks by identifying the entry points of the pedicles.

Then, with the aid of X-rays taken at the time of diagnosis, he evaluates the position of the pedicles, their orientation and the condition of the internal structures in order to orient his ballistic angle, i.e. the angle at which he will penetrate the pedicles.

The surgeon then proceeds to penetrate the positions (location, angle, depth) that he has determined. This is done with the aid of a "Trocar" comprising a rod with a trocar tip capable of penetrating the bone, and a cannula (or liner) consisting of a tube within which the rod slides. The cannula and rod are provided with a handle for gripping.

Once the bone has been penetrated, he removes the rod and leaves the cannula in place to control penetration.

This control is usually achieved with the aid of an image intensifier (fluoroscopy).

If the penetration is correct, the surgeon removes the cannula, then inserts the pedicle screws down the hole, creating a tapped portion in the bone. If the latter is brittle or if there should be a slight twisting movement, the bone can crack or even rupture. Furthermore, the screw may not perfectly follow the hole previously made with the trocar.

Once the pedicle screws are fixed, the surgeon positions the curvature rods and reinforcement rods and fixes them in position.

The entire operation requires a large space in order to allow sufficient room for the surgeon to screw in the pedicle screws, bend the curvature rods and finally position the curvature rods and reinforcement rods.

However, in the event of a complex anatomy or severe deformation of the spinal column (for example in the event of rotation of the thoracic region), the image intensifier is insufficient and gives rise to considerable radiation.

It is then necessary to use other types of assistance tools.

For instance, so-called computerized "navigation" systems are known with prior recalibration of the scanner images thanks to the image intensifier. However, they can be unreliable and unwieldy. In fact, the scanner images are taken with the patient lying on his back, whereas the intervention must be performed with the patient lying on his stomach.

Furthermore, the anatomical points measured to readjust the images require long sequences of topographical measurements without achieving absolute precision, because the spine is an articulated system that is movable between each of its elements, and so likely to change its position albeit only as a result of respiratory movements.

O-Arm type scanners are also known, offering precise measurements that enable some of these drawbacks to be overcome, but their size, the time required to set them up, the difficulty of preparing the surgical site, taking scanner images and performing surgical procedures make their use very delicate and cumbersome. Moreover, the protection of personnel (surgeon, anesthetist, nursing staff and operation assistants) during the intervention complicates the repetitive use of this equipment when instrumentation is required along the full length of the spinal column. Asepsis problems also arise with this type of mapping on a patient undergoing open surgery.

It is also proposed to use a robot to screw in the pedicle screws.

However, this type of robot requires millimetric precision with an accuracy of one degree, with recurrent recalibrations as you move away from the pelvis. Here again, the rotation of the vertebral bodies is a major hurdle for the reliability of the system, particularly in the thoracic region. The need for an O-Arm operating scanner associated with the robot makes the general size a hindrance to performing this surgical procedure. Furthermore, the need to have a carbon operating table increases the already very high equipment cost.

The aim of the present invention is to propose an economical and very accurate device, enabling the implementation of an affordable, original and safe technical procedure that reduces exposure to surgery.

The invention enables markedly improved safety (improvement of the general asepsis of the operation and reduction of bleeding, neurological risk and operating complications), limitation to exposure to radiation, optimal positioning of implants including in regions not exploited until now, by combining mini-invasive surgery and interventional radiology by scanner.

Thus, the invention proposes to divide the operation into two separate phases: one in the radiology room, the other in the operating room.

For this, the invention proposes a temporary-use locator pin, as well as a system for the insertion and removal of said locator-pin, to enable the passage between the phase in the radiology room and the operating phase in the operation room whilst improving the precision of positioning the pedicle screws thanks to optimum exchange of information between the radiologist and the surgeon.

To this end, the invention relates to a system for the insertion and removal of a locator pin for positioning a pedicle screw in a bone, the system comprising:
   a locator-pin comprising:
      a pin body;
      a distal portion shaped so as to penetrate a bone; and
      a proximal portion equipped with:
         a first fixing member to fix, during use, to an insertion pin-carrier; and
         a second fixing member to fix, during use, to a removal pin-carrier; the two fixing members being different;
   an insertion pin-carrier equipped with a fixing member complementary to the first fixing member of the locator-pin;
   a removal pin-carrier equipped with a fixing member complementary to the second fixing member of the locator-pin; and
   a guide cannula designed to receive freely sliding the locator-pin, the insertion pin-carrier and the removal pin-carrier.

The invention also relates to a locator pin for positioning a pedicle screw in a bone, comprising:
   a pin body;
   a distal portion shaped so as to penetrate a bone; and
   a proximal portion equipped with:
      a first fixing member to fix, during use, to the insertion pin-carrier; and
      a second fixing member to fix, during use, to the removal pin-carrier; the two fixing members being different;

According to particular embodiments:
   the first fixing member may be a radial locking member of the insertion pin-carrier on the locator-pin, and the second fixing member is an axial locking member, parallel to the locator-pin, of the removal pin-carrier on the locator-pin;
   the first fixing member may be of the bayonet type and the second fixing member is of the threaded type;
   the first fixing member of the bayonet type may comprise a lug arranged radially on the proximal portion of the locator-pin, and designed to slide axially, during use, in a groove located in the insertion pin-carrier; and the second fixing member may be a threaded portion arranged on the proximal portion of the locator-pin, between the first fixing member and a proximal end of the locator-pin, and designed to be screwed, during use, into a tapped hole located in the removal pin-carrier;
   the first fixing member of the bayonet type may comprise a groove arranged on the proximal portion of the pin, and designed to receive, during use, a lug arranged radially in a cavity located in the insertion pin-carrier; and the second fixing member may be a threaded portion arranged on the proximal portion, between the first fixing member and a proximal end of the locator-pin, and designed to be screwed, during use, into a tapped hole located in the removal pin-carrier; and/or
   a flat surface may be provided between the proximal part and the pin body.

The invention also relates to an insertion pin-carrier of a locator-pin described here above, the insertion pin-carrier comprising:
   a cylindrical body;
   a proximal end equipped with a gripping handle;
   a distal end equipped with:
      a groove designed to receive, during use, the lug located in the insertion pin-carrier, the groove being arranged to enable radial locking of the lug; and
      a tubular cavity designed to receive sliding freely, during use, the threaded portion located on the locator-pin.

The invention also relates to an insertion pin-carrier of a locator-pin described here above, the insertion pin-carrier comprising:
   a cylindrical body;
   a proximal end equipped with a gripping handle;
   a distal end equipped with:
      a tubular cavity designed to receive sliding freely, during use, the threaded portion located on the locator-pin; a lug arranged radially in the tubular cavity and designed to engage, during use, in the groove arranged on the proximal end of the pin-carrier to enable radial locking of the lug.

The invention also relates to a removal pin-carrier of a locator-pin described here above, the removal pin-carrier comprising:
   a cylindrical body;
   a proximal end equipped with a gripping handle;
   a distal end equipped with a tapped hole designed to be screwed, during use, onto the threaded portion located on the locator-pin.

The invention also relates to a system for inserting and removing described here above, the system comprising:
   a locator-pin described here above;
   an insertion pin-carrier described here above; and
   a removal pin-carrier described here above.

The invention also relates to a method for inserting a locator pin for positioning a pedicle screw in a vertebrae of a patient, comprising:
   providing the locator pin, insertion pin-carrier, and guide cannula of a system described here above;
   positioning the cannula 140 on the skin S of the patient;
   inserting into the cannula 140 the locator-pin 110-210 fixed to the insertion pin-carrier 120 by the first fixing member;
   piercing the skin S of the patient with the trocar tip 114 of the locator-pin 110-210 and inserting the assembly up to the surface of the vertebrae O;
   inserting the locator-pin into the axis of the pedicle to ensure passage through the cortical layer;
   driving the locator-pin 110-210, fixed to the pin-carrier 120-220 by the first fixing member 118 and slid into the cannula 140 into the axis of the pedicle of the vertebra O to thereby place the locator-pin;
   disengaging the first fixing member 118 and removing the insertion pin-carrier 120 and the cannula 140 to thereby provide the inserted locator pin.

The invention also relates to a method for recovering a positioned locator pin from a patient, comprising:
   providing a removal pin-carrier 130 of a system described here above;
   making an incision to disengage the head of a positioned locator pin;
   reinserting the cannula 140, encasing the locator-pin and following its path into the pedicle of vertebra O;
   introducing the removal pin-carrier 130 into the cannula 140 and screwing onto the threaded end of the locator-pin 110 to secure the locator pin;
   removing the locator pin through the hole in the cannula 140, which is left in place.

The invention also relates to a method for fixing a pedicle screw into the vertebra of a patient, comprising:

providing the locator pin, insertion pin-carrier, removal pin-carrier, and guide cannula of a system described here above;

positioning the cannula 140 on the skin S of the patient;

inserting into the cannula 140 the locator-pin 110-210 fixed to the insertion pin-carrier 120 by the first fixing member;

piercing the skin S of the patient with the trocar tip 114 of the locator-pin 110-210 and inserting the assembly up to the surface of the vertebrae O;

inserting the locator-pin into the axis of the pedicle to ensure passage through the cortical layer;

driving the locator-pin 110-210, fixed to the pin-carrier 120-220 by the first fixing member 118 and slid into the cannula 140 into the axis of the pedicle of the vertebra O to thereby place the locator-pin;

disengaging the first fixing member 118 and removing the insertion pin-carrier 120 and the cannula 140 to thereby provide the inserted locator pin;

making an incision to disengage the head of a positioned locator pin;

reinserting the cannula 140, encasing the locator-pin and following its path into the pedicle of vertebra O;

introducing the removal pin-carrier 130 into the cannula 140 and screwing onto the threaded end of the locator-pin 110 to secure the locator pin;

removing the locator pin through the hole in the cannula 140, which is left in place;

inserting a guide rod and removing the cannula;

fixing the pedicle screw.

Other features of the invention are outlined in the following detailed description, given with reference to the accompanying drawings, which represent, respectively:

FIGS. 1a to 1d are schematic perspective views of a system for the insertion and removal of a so-called "locator" pin according to the invention comprising, in FIG. 1a, a first embodiment of a locator-pin according to the invention, in FIG. 1b, a first embodiment of an insertion pin-carrier according to the invention, in FIG. 1c, a removal pin-carrier according to the invention and, in FIG. 1d, a guide cannula;

FIG. 2 is a schematic perspective view of a second embodiment of a locator-pin according to the invention;

FIG. 3 is a schematic perspective view of a second embodiment of an insertion pin-carrier according to the invention;

FIGS. 4 to 8 are schematic sectional views of the method of implementing a system according to the invention to insert a locator-pin according to the invention before operation;

FIGS. 9 to 14 are schematic sectional views of the method of implementing the system according to the invention to remove a locator-pin according to the invention during the operation and to position a pedicle screw;

FIG. 15 is a schematic plan view of a cannulated pedicle screw; and

FIG. 16 is a schematic plan view of the pedicle screw shown in FIG. 15 equipped with an extension tube.

FIG. 1 shows a system 100 for the insertion and removal of a locator pin 110 for positioning a pedicle screw in a bone.

The system 100 comprises a locator-pin 110 (FIG. 1a), an insertion pin-carrier 120 (FIG. 1b), a removal pin-carrier 130 (FIG. 1c) and a guide cannula 140 (FIG. 1d).

According to the invention, the locator-pin 110 comprises:

a pin body 112;

a distal portion 114 shaped so as to penetrate a bone (for example a trocar point); and a proximal portion 116 equipped with:
  a first fixing member 118 to fix, during use, to the insertion pin-carrier 120; and
  a second fixing member 119 to fix, during use, to the removal pin-carrier 130.

According to the invention, the two fixing members 118 and 119 are different, the insertion pin-carrier 120 is equipped with a fixing member 121 complementary to the first fixing member 118 of the locator-pin 110, and the removal pin-carrier 130 is equipped with a fixing member 131 complementary to the second fixing member 119 of the locator-pin 110.]

The first fixing member 118 of the locator pin and the fixing member 121 of the insertion pin-carrier enable, basically, the rotatable connection of the insertion pin-carrier 120 to the locator-pin during the insertion of said locator-pin into the bone. This insertion can be achieved by percussion, thanks to a hammer, but also by screwing the locator-pin into the bone. In the latter case, the rotatable connection of the pin-carrier 120 to the locator-pin 110 enables a torque to be transmitted between the insertion pin-carrier 120 and the locator-pin 110.

The first fixing member 118 of the locator pin and the fixing member 121 of the insertion pin-carrier also enable the dismantling of the insertion pin-carrier 120 and locator-pin 110 when the latter is in position in the bone.

The second fixing member 119 of the locator pin and the fixing member 131 of the removal pin-carrier enable, basically, the translational connection of the removal pin-carrier 130 to the locator-pin 110 during the removal of said locator-pin 110 from the bone. This removal must not damage the bone and, above all, the hole made during the insertion. The translational locking must therefore be firm and precise. Since the traction required to remove the locator-pin can be great, the second fixing member must be strong and must not risk being damaged on removal.

Thus, the first fixing member 118 is a radial locking member of the insertion pin-carrier 120 on the locator-pin 110, and the second fixing member 119 is an axial locking member (i.e. parallel to the longitudinal direction of the slim body 112 of the locator-pin 110) of the removal pin-carrier 130 on the locator-pin 110.

Advantageously, the first fixing member 118 is of the bayonet type and the second fixing member 119 is of the threaded type.

In the embodiment shown in FIG. 1a, the first fixing member 118 comprises a lug arranged radially on the proximal portion 116 of the locator-pin and the fixing member 121 of the insertion pin-carrier comprises a groove located in the distal end of the insertion pin-carrier 120. The first fixing member 118 of the locator pin is designed to slide axially, during use, in the member 121 of the insertion pin-carrier.

The second fixing member 119 is a threaded portion arranged on the proximal portion 116, between the first fixing member (lug) 118 (and a proximal end 116a of the locator-pin 110.

The second fixing member (threaded portion) 119 is designed:

to be inserted sliding freely in a tubular cavity 122 of the insertion pin-carrier during the insertion of the locator-pin into the bone;

to be screwed, to remove the locator-pin, into the fixing member 131 (tapped hole) of the removal pin-carrier 130.

Thus, on insertion, the threaded portion 119 is protected from the hammer blows received by the insertion pin-carrier 120. On removal, it is screwed into the tapped hole 131 in order firmly and precisely to connect the removal pin-carrier 130 on the locator-pin 110. The numerous contact points between the threaded portion and the tapped portion ensure a precise positioning and a wide distribution of the traction forces, thus reducing the risk of damaging the second fixing member on removal.

The first fixing member 118 enables the insertion of the locator-pin by "screwing" into the bone. In order to protect the first fixing member 118 in the event of insertion by percussion, a flat surface 115 is provided between the proximal part 116 and the pin body 112. This flat surface 115 is arranged to be in contact with the distal end edge 124 of the insertion pin-carrier 120.

The dimensions of the groove 121 and the cavity 122 are chosen so that the lug 118 is not in contact with the edges of the groove 121 and so that the proximal end of the locator-pin is not in contact with the bottom of the cavity 122 when the distal end edge 124 of the insertion pin-carrier 120 is in contact with the flat surface 115. Thus, it is in fact the latter that undergoes all of the percussion shocks of the hammer.

The cylindrical body of the insertion pin-carrier 120 also comprises, at its proximal end, a gripping handle 126.

To remove the locator-pin, the surgeon uses the removal pin-carrier 130 which comprises:
 a cylindrical body 132;
 a proximal end equipped with a gripping handle 133; and
 a distal end equipped with a fixing member 131 (tapped hole) designed to be screwed, on removal, onto the threaded portion 119 located on the locator-pin 110.

Thus, the surgeon screws the removal pin-carrier until both the proximal end of the locator-pin comes into contact with the bottom of the tapped hole 131 and the edge of the distal end of the removal pin-carrier 130 comes into contact with the lug 118 of the locator-pin.

He can then pull on the gripping handle 133 to remove the locator-pin from the bone.

Clearly, in order to guide both the insertion and removal of the locator-pin, the system according to the invention comprises a guide cannula 140 designed to receive freely sliding the locator-pin 110, the insertion pin-carrier 120 and the removal pin-carrier 130.

For this purpose, the guide cannula 140 comprises an internal channel 141 running through the cannula 140 from one end to the other. The cannula also comprises a gripping handle 142, advantageously having a shape complementary to the handle 126-133 of the pin-carriers 120-130 to enable locking onto the cannula.

FIGS. 2 and 3 show a second embodiment of a locator-pin 210 and an insertion pin-carrier 220 according to the invention.

In a second embodiment, first fixing member 218 of the bayonet type comprises a groove arranged on the proximal portion 216 of the locator-pin 210, and the fixing member 222 of the insertion pin-carrier comprises lug arranged radially in a cavity 224 located in the insertion pin-carrier 220.

The insertion pin-carrier 220 of this second embodiment of the location pin thus comprises:
 a cylindrical body 226;
 a proximal end equipped with a gripping handle 228;
 a distal end equipped with:
  a tubular cavity 224 designed to receive sliding freely, during use, the threaded portion 119 located on the locator-pin 210;
  a lug 222 arranged radially in the tubular cavity 224 and designed to engage, during use, in the slot 218 arranged on the proximal portion 216 of the locator-pin 210 to enable radial locking of the lug 222.

The second fixing member is also a threaded portion arranged on the proximal portion of the locator-pin, between the groove (the first fixing member) and the proximal end of the locator-pin. The removal pin-carrier to remove the locator-pin according to this second embodiment is similar to that shown in FIG. 1c.

FIGS. 4 to 14 show the method of implementation enabled by the system of locator-pins according to the invention.

First of all, the surgeon produces an implantation diagram of the pedicle screws, based on the scans of the spine in the coronal and sagittal plane, to be submitted to the radiology team.

Since the risk of damage to the spinal cord is almost completely reduced, the system according to the invention enables implants to be placed where previously it was impossible to do so (for example at the top of the concavity). The surgeon can therefore define the locations of the screws so as to optimize the correction. The determination of these locations obeys precise anatomical and biomechanical rules, although adjustment may be necessary in order to take into account the singularities of a patient.

The first step involves mapping the "key vertebrae" of the assembly: the apical vertebra and the most inclined vertebrae.

The surgeon then identifies the vertebrae at the ends of the assembly: these vertebrae must as far as possible be located two or three levels above or below the most inclined vertebrae. The choice of the bottom vertebra of the assembly is made by leaving, if possible, at least two or three free discs beneath the assembly.

The two extreme vertebrae must be on the same vertical plane seen from the front, the axis towards which the correction must aim.

It is imperative that the profile dorsal curvature be taken into account: the assembly must not stop at the top of a sagittal curvature.

Lastly, the assembly must not stop at the thoraco-lumbar junction, the area of maximum stress between the fixed region and the region that remains mobile, but must on the contrary lock it by including at least vertebrae L1 or L2.

The surgeon then produces an implantation diagram for the radiologist who is to position the locator-pins 110.

FIGS. 4 to 8 show the insertion of the locator-pin 110.

In the embodiment, vertebra O has a torsion of angle α between its X-X' axis and the vertical V, a torsion that must be reduced until the angle α is substantially equal to 0.

The patient under general anesthetic is on the table of the scanner, which can be controlled by a joystick. By following the indications given by the surgeon in the implantation diagram, the radiologist locates on a full scan of the spine the pedicles to be instrumented and maps the corresponding cuts in order to locate directly the control position of the scanner during the procedure. He draws on the image the axis of the pedicle and checks the feasibility of installing implants.

The precision mapping of the pedicles by using a scanner considerably reduces the operation risk.

The installation of locating pins by using a scanner imposes a certain number of essential conditions for the proper operation of the procedure. The scanner room becomes an operating room like any operating procedure using a scanner. Prior cleaning, as with any operating room, asepsis of the operating area, sterilization of the equipment and preparation of the radiology team for an operating procedure are essential. Anesthesia for any surgical intervention begins here. The equipment, fluids, respirator and anesthesia trolley, as well as the presence of an anesthetist, are essential throughout this procedure.

In order to position the locator-pin 110-210, in the same way that he targets his pedicle when performing a cementoplasty for example, the operating radiologist positions the cannula 140 on the skin S of the patient (FIG. 4). Then he inserts into the cannula 140 the locator-pin 110-210 fixed to the insertion pin-holder 120 by the first fixing member (arrows F1-F2).

The operating radiologist then pierces the skin S of the patient with the trocar tip 114 of the locator-pin 110-210 and inserts the assembly up to the surface of the vertebrae O.

By pressure/rotation (arrows F3-F4; FIG. 5) by hand or with a hammer, the operating radiologist inserts the locator-pin into the axis of the pedicle to around 10 mm to ensure passage through the hard outer surface, formed of compact bone, called the cortical layer.

Alternatively, in order to pierce the skin and the cortical layer, the operating radiologist can use, instead of the locator-pin/insertion pin-carrier, a simple Jamshidi-type trocar rod with a Jamshidi-type cannula 140. In this case, he must then remove the trocar needle, leaving in place the cannula 140 that surrounds it and serves as a target guide to install the locator-pin/insertion pin-carrier assembly.

The locator-pin 110-210, fixed to the pin-carrier 120-220 by the first fixing member 118 and slid into the cannula 140, is then driven into the axis of the pedicle of each vertebra O to be instrumented (and as far as possible parallel to the vertebral endplate) with a hammer or with the aid of a micromotor, depending on the mapping performed and checked by a scanner in real time (arrows F3-F4; FIG. 5).

The penetration depth (P approximately 50 to 60 mm) of the locator-pin 110-210 is measured to determine the length of the pedicle screw to be used (L=P−1 cm).

Once the locator-pin is in place, the first fixing member 118 is disengaged in order to remove the insertion pin-carrier 120 and the cannula 140.

In the embodiment shown, this is done by performing a rotation/translation movement on the handle (arrows F5-F6) if the groove 121 is L-shaped, or by a simple translation movement if the groove is straight and serves only to prevent rotation between the insertion pin-carrier 120 and the locator-pin 110.

The length of the locator-pins 110-210 installed is chosen so that the threaded end is just under the skin and can be palpated for easy localization (FIG. 8).

When all of the locator-pins are in place, the patient is taken to the operating room, accompanied by a transmission log completed by the radiologist and given to the surgeon. This log comprises a report on the intervention, indicating any anomalies, as well as a series of scanner images showing all of the instrumented vertebrae in axial view, plus a general front and profile view. This enables the surgeon to compare the actual implantation of the locator-pins with his intervention diagram and ensure that the operating procedures are feasible.

FIGS. 9 to 14 show the operating phase of installing pedicle screws and corrective rods.

Placing the patient on the operating table ensures that no spurious constraint will distort the correction.

The patient is installed on the operating table in a prone position, with no external stress: in particular, no traction. The aim is to effect the correction from a position that is "natural" or relaxed and above all not pre-stressed.

The patient is accompanied by his "transmission log," together with scanner slices and general views to enable the positioning to be checked. This log takes the place of documentation for the file.

The intervention is mini-invasive because the incisions can be limited to the minimum necessary to disengage the heads of the locator-pins 110.

The first surgical procedure is to recover the locator-pins 110 while of course preserving the "pedicle's ballistic path" in order to insert cannulated pedicle screws.

The insertion point of the locator-pins 110 is located visually and by palpation.

For each locator-pin, the surgeon makes a 16- to 18-mm incision to disengage the head. The incision is made opposite the subcutaneous projection of the pin of which the initial penetration hole is also visible on the skin (see FIG. 8). The incision can be single or elongated for two contiguous locator-pins 110. The superficial end of the locator-pin 110 having thus been identified, the cannula 140 is reinserted (arrow F7; FIG. 9) encasing the locator-pin and following its path into the pedicle of vertebra O.

A removal pin-carrier 130 is then introduced into the cannula 140 (arrow F8; FIG. 9) and screwed onto the threaded end of the locator-pin 110 (arrow F9; FIG. 10). Thus secured, the locator-pin 110 is removed through the hole in the cannula 140, which is left in place.

In place of the locator-pin, a flexible guide-rod 150 (Kirschner wire) is slid into the cannula 140 (FIG. 11), which is then carefully removed.

The locator-pins 110 are replaced by guide-rods that ensure a perfect pedicle target. A guide to insert the pedicle screws is then in place along the path created in the pedicle by the locator-pins 110 installed when mapping by radiology using a scanner.

In order to keep the tissues apart and allow instruments to pass into the pedicle, a first dilator tube 160 is placed around the guide-rod 150 until contact is made with the pedicle (FIG. 12).

In practice, the dilator tube consists of several coaxial tubes of increasing diameters. Thus, a first small-diameter tube is inserted round the guide-rod, then a second larger-diameter tube, around the first, then a third even larger-diameter tube around the second.

The surgeon then takes an advantageously cannulated pedicle screw 170 (FIG. 15), i.e. with a central or lateral channel 171 of sufficient diameter to receive the guide-rod 150.

On insertion and reduction of the torsion, the pedicle screw 170 is fixed to the end of a tubular extension 172 (FIG. 16).

In order to facilitate the passage of the pedicle screw 170 through the cortical layer, a cannulated square tip guided by the dilator tube can be used.

In the axis of the guide-rod 150 and thus of the pedicle, a starter hole can advantageously be tapped to facilitate the passage of the screw 170.

Fixed to the end of a tubular extension 172, the pedicle screw 170 is guided by the guide-rod 150 to the starter hole into which it is screwed to the desired depth. The guide-rod 150 can be removed as soon as the screw is properly engaged in the pedicle.

The extension tubes can be left in place to act as handles that will enable the position of the vertebrae to be adjusted, as shown in FIG. 14.

The surgeon reduces the torsion of the vertebra either by hand or with the aid of a dedicated tool until the axis X-X' of the vertebra is vertical, in the case shown.

The vertebra is thus held in place thanks to a correction rod 180.

In further detail, this straightening operation is performed in several steps.

Firstly, the most inclined vertebrae are rendered horizontal thanks to an angle correction device (for example Marnay's Angle Corrector): this type of device, used in the case of extreme curvatures that are difficult to reduce, enables, thanks to a double rack on the concave side and on the convex side, the overall curvature between the two most inclined vertebrae to be corrected and to maintain this correction until rods are installed.

Then vertebral distraction is performed in the case of pronounced narrowing.

The action of the distractor, compared to that of the horizontalizer, is local and lateral, at the segmental level. It enables significant narrowing between two consecutive vertebrae to be corrected.

Once the angle corrections have been made, the correction rods: curvature rods and reinforcement rods, are positioned.

Titanium curvature rods are relatively flexible in order to facilitate their insertion and obtain a first reduction of scoliosis without excessive stress.

Chrome-cobalt reinforcement rods are more rigid than the correction rods that they complement and fix the corrective effect.

All correction rods must be bent so as to anticipate the target sagittal curvature (dorsal lordosis) whilst matching as closely as possible the frontal curvature to be corrected.

Bending the concave curvature rod facilitates its insertion into the screw heads, then gives the spine the desired sagittal curvature while reducing the frontal curvature when, once installed, the rod is pivoted 90°, so that its curvature passes from the frontal plane to the sagittal plane.

The relative flexibility of a titanium rod enables its curvature to be increased, at the same time the reduction of the vertebral curvature is begun, in order to marry it up with the heads of the pedicle screws.

The rods are installed as described below.

The first rod to be installed is the curvature rod on the concavity side. Before being inserted, this rod must be bent so as to anticipate the target sagittal curve (kyphosis and dorsal lordosis) while matching up as closely as possible with the frontal curvature to be corrected; it is also cut to the correct length.

Held by a gripper, the concave curvature rod is introduced percutaneously, from the top downwards (in the craniocaudal direction), by manipulating the extension tubes to place the tulip of the screw head opposite the end of the rod.

It is sometimes necessary to widen an incision in order to insert the rod.

Note that it may be preferable to insert the rod from the bottom upwards, i.e. by starting from the pelvis, which is the natural reference point. But lumbar lordosis and the buttocks are a hindrance to introducing the rod, whereas the head, being narrower and inclined forwards, is much less so.

When the rod is inserted into the pedicle screw head, the lock nut is fitted but not tightened up: it is in fact essential to maintain maximum freedom in the adjustment of the position of the vertebrae until the end of the intervention so as to optimize the correction.

The convex curvature rod is then introduced just after the concave curvature rod; it will serve as a counter-brace facilitating the maneuvers of "derotation" and horizontalization of the vertebrae.

Once the two correction rods have been installed, the concave curvature rod is pivoted 90° about its main axis which, together with an action on the extension tubes, forces the derotation and horizontalization of the vertebrae.

This rotation is controlled by the rod gripper, whose fixing plane must coincide with the bending plane, bending that ultimately determines the antero-posterior curvature of the spine. Thus, when the gripper is perpendicular to the patient's back, we will know that the rotation performed is indeed 90°.

Once the concave curvature rod has been turned 90°, it can be fixed by tightening the nut on the pedicle screw head of the top vertebra of the assembly. No other screw head will be tightened at this stage in order to allow the rod to slide without further stress until the reduction of the curvature has been completed.

After the concave curvature rod has been turned 90°, the convex curvature rod is turned 90° in its turn and in the same way, which perfects the correction.

Once the rods are engaged in the screws, two specific cases can arise: the resilient return force of the rods overrides that of the spine, or vice versa.

If the return force of the rod is greater than that of the spine, on regaining its original shape, the rod further reduces the vertebral curvature. Then the 90° rotation of the rod further reduces the curvature, which is completed by installing the convex rod.

If the return force of the rod is less than that of the spine, the rod only partially restores the curvature of the spine. And even after the 90° rotation, the rod stays curved in the frontal plane. In these conditions, the convex rod also does not succeed in reducing the curvature of the spine. Reinforcement rods are therefore required.

In this case, on the concavity side the correction of the curvature is reinforced; on the convexity side the correction of the torsion manifested by gibbosity is reinforced.

Each of these two rods is mounted on three of four lateral connectors fixed to correction rods. The first reinforcement rod is located on the concavity side to fix the preliminary reduction ensured by the correction rod. The second reinforcement rod, located on the convexity side, serves to maintain a rotation torque that corrects the gibbosity.

As the rods installed still have a certain freedom of movement, the correction can be adjusted before the nuts are gradually tightened.

It must be possible to move everything for as long as possible in order to be able to adjust and optimize the reduction of the scoliosis. When everything is in place, only then can the assembly be locked in position by tightening the nuts of the pedicle screws and connectors.

A bone graft was absolutely essential in the conventional state of the art (as was fitting a Harrington rod) in order for vertebral fusion to compensate for the considerable stress exerted on the assembly.

Thanks to the system according to the invention, it is possible to equip vertebrae that until now have never been equipped, which enables a better reduction of the curvature, an optimization of the distribution of loads on four rods and the preservation of the muscle structure.

All this makes grafting less essential, but enables the anchorages to be secured and the fusion of the vertebrae to be accelerated, particularly in the "hinge regions," i.e. in the regions of change in stress.

Along the entire length of the fusion rods, after having squared up the cross-pieces, grafts are then injected: bank bone or bone substitute (hydroxyapatite), plus bone marrow.

Thanks to the system according to the invention, the precision of implantation of the locator-pins almost totally reduces the risk of following the wrong path and intruding into the medullar canal.

As the open time and exposure surface are extremely reduced compared to conventional techniques, the risk of infection is equally reduced.

The mini-invasive nature of the intervention practically eliminates any risk of hemorrhage.

Lastly, the damage to the dorsal muscles is minimal and does not affect their capacity to support the spinal column; there is no risk of muscle necrosis.

The system according to the invention enables the operation to be divided in two: one phase in the radiology room and one phase in the operating room.

This limits the exposure of the medical staff to radiation. In fact, in the conventional procedure, all operating theater personnel (four to five people) are exposed to radiation, whereas with the procedure allowed by the system according to the invention, only the personnel in the radiology room (two people) are exposed.

On an economic level, the procedure enabled by the system according to the invention is very advantageous since the scanner it uses in the radiology room is the same as those that exist in any hospital, a scanner whose use is not reserved solely for this purpose and which can therefore operate continuously for very diverse applications.

This is to be compared with the use of an intraoperative scanner like the O-ARM, whose use is substantially more limited and whose current price is around 1 million euros, to which must be added that of a carbon table at around 400,000 euros.

Moreover, although the duration of the "overall" intervention (radiology+surgery) is more or less equivalent to that of a traditional technique, the time spent in the operating theater is reduced by half. Considering that two people are required in radiology and four or five in theater, making a total intervention time of 6 hours, the saving is 6 to 9 h of personnel time.

Causing the minimum amount of trauma, an intervention using a system according to the invention is followed by a rapid convalescence requiring less post-operative care.

The invention includes the following non-limiting embodiments. These embodiments are provided as examples only and do not limit the scope of the invention.

Embodiment 1

A system (100) for the insertion and removal of a locator pin (110-210) for positioning a pedicle screw (170) in a bone (O), comprising:
 a locator-pin (110-210) comprising:
  a pin body (112);
  a distal portion (114) shaped so as to penetrate a bone; and
  a proximal portion (116) equipped with:
   a first fixing member (118) to fix, during use, to an insertion pin-carrier (120); and
   a second fixing member (119) to fix, during use, to a removal pin-carrier (130);
   the two fixing members (118, 119) being different;
 an insertion pin-carrier (120) equipped with a fixing member (121) complementary to the first fixing member (118) of the locator-pin;
 a removal pin-carrier equipped with a fixing member (131) complementary to the second fixing member (119) of the locator-pin; and
 a guide cannula (140) designed to receive freely sliding the locator-pin (110), the insertion pin-carrier (120) and the removal pin-carrier (130).

Embodiment 2

A locator pin (110-210) for positioning a pedicle screw in a bone, comprising:
 a pin body (112);
 a distal portion (114) shaped so as to penetrate a bone; and
 a proximal portion (116) equipped with:
  a first fixing member (118) to fix, during use, to the insertion pin-carrier (120); and
  a second fixing member (119) to fix, during use, to the removal pin-carrier (130);
 the two fixing members (118, 119) being different.

Embodiment 3

The locator pin (110-210) according to embodiment 2, wherein the first fixing member (118) is a radial locking member (of the insertion pin-carrier (120) on the locator-pin (110), and the second fixing member (119) is an axial locking member, parallel to the locator-pin, of the removal pin-carrier (130) on the locator-pin (110).

Embodiment 4

The locator pin (110-210) according to embodiment 3, wherein the first fixing member is of the bayonet type and the second fixing member is of the threaded type.

Embodiment 5

The locator pin (110) according to embodiment 4, wherein:
 the first fixing member of the bayonet type comprises a lug (118) arranged radially on the proximal portion (116) of the locator-pin, and designed to slide axially, during use, in a groove (121) located in the insertion pin-carrier (120); and
 the second fixing member is a threaded portion (119) arranged on the proximal portion (116) of the locator-pin, between the first fixing member (118) and a proximal end of the locator-pin, and designed to be screwed, during use, into a tapped hole (131) located in the removal pin-carrier (130).

Embodiment 6

The locator pin (210) according to embodiment 4, wherein:
 the first fixing member of the bayonet type comprises a groove (218) arranged on the proximal portion (216) of the pin, and designed to receive, during use, a lug (222) arranged radially in a cavity (224) located in the insertion pin-carrier (220); and
 the second fixing member is a threaded portion (119) arranged on the proximal portion (216), between the first fixing member (218) and a proximal end of the locator-pin, and designed to be screwed, during use, into a tapped hole (131) located in the removal pin-carrier (130).

Embodiment 7

The locator pin (110-210) according to any of embodiments 2 to 6, wherein a flat surface (115) is provided between the proximal part and the pin body.

Embodiment 8

An insertion pin-carrier (120) of a locator pin comprising:
a cylindrical body;
a proximal end equipped with a gripping handle (126);
a distal end (124) equipped with:
- a groove (121) designed to receive, during use, a lug (118) located in a locator pin (110), the groove (121) being arranged to enable radial locking of the lug (118); and
- a tubular cavity (122) designed to receive sliding freely, during use, a threaded portion (119) located on the locator-pin.

Embodiment 9

An insertion pin-carrier (220) of a locator-pin (210) comprising:
a cylindrical body (226);
a proximal end equipped with a gripping handle (228);
a distal end equipped with:
- a tubular cavity (224) designed to receive sliding freely, during use, the threaded portion (119) located on a locator-pin (210);
- a lug (222) arranged radially in the tubular cavity (224) and designed to engage, during use, in the groove (218) arranged on the proximal end (216) of the pin-carrier (210) to enable radial locking of the lug (222).

Embodiment 10

A removal pin-carrier of a locator-pin (110-210) comprising:
a cylindrical body (132);
a proximal end equipped with a gripping handle (133);
a distal end equipped with a tapped hole (131) designed to be screwed, during use, onto the threaded portion (119) located on a locator-pin (110-210).

Embodiment 11

A system for inserting and removing according to embodiment 1, comprising:
a locator-pin according to any of embodiments 2 to 7;
an insertion pin-carrier according to any of embodiments 8 or 9; and
a removal pin-carrier according to embodiment 10.

Embodiment 12

A method for inserting a locator pin for positioning a pedicle screw in a vertebrae of a patient, comprising:
providing the locator pin, insertion pin-carrier, and guide cannula of a system according to embodiment 1;
positioning the cannula 140 on the skin S of the patient;
inserting into the cannula 140 the locator-pin 110-210 fixed to the insertion pin-carrier 120 by the first fixing member;
piercing the skin S of the patient with the trocar tip 114 of the locator-pin 110-210 and inserting the assembly up to the surface of the vertebrae O;
inserting the locator-pin into the axis of the pedicle to ensure passage through the cortical layer;
driving the locator-pin 110-210, fixed to the pin-carrier 120-220 by the first fixing member 118 and slid into the cannula 140 into the axis of the pedicle of the vertebra O to thereby place the locator-pin;
disengaging the first fixing member 118 and removing the insertion pin-carrier 120 and the cannula 140 to thereby provide the inserted locator pin.

Embodiment 13

A method for recovering a positioned locator pin from a patient, comprising:
providing a removal pin-carrier 130 of the system according to embodiment 1;
making an incision to disengage the head of a positioned locator pin;
reinserting the cannula 140, encasing the locator-pin and following its path into the pedicle of vertebra O;
introducing the removal pin-carrier 130 into the cannula 140 and screwing onto the threaded end of the locator-pin 110 to secure the locator pin;
removing the locator pin through the hole in the cannula 140, which is left in place.

Embodiment 14

A method for fixing a pedicle screw into the vertebra of a patient, comprising:
providing the locator pin, insertion pin-carrier, removal pin-carrier, and guide cannula of a system according to embodiment 1;
positioning the cannula 140 on the skin S of the patient;
inserting into the cannula 140 the locator-pin 110-210 fixed to the insertion pin-carrier 120 by the first fixing member;
piercing the skin S of the patient with the trocar tip 114 of the locator-pin 110-210 and inserting the assembly up to the surface of the vertebrae O;
inserting the locator-pin into the axis of the pedicle to ensure passage through the cortical layer;
driving the locator-pin 110-210, fixed to the pin-carrier 120-220 by the first fixing member 118 and slid into the cannula 140 into the axis of the pedicle of the vertebra O to thereby place the locator-pin;
disengaging the first fixing member 118 and removing the insertion pin-carrier 120 and the cannula 140 to thereby provide the inserted locator pin;
making an incision to disengage the head of a positioned locator pin;
reinserting the cannula 140, encasing the locator-pin and following its path into the pedicle of vertebra O;
introducing the removal pin-carrier 130 into the cannula 140 and screwing onto the threaded end of the locator-pin 110 to secure the locator pin;
removing the locator pin through the hole in the cannula 140, which is left in place;
inserting a guide rod and removing the cannula;
fixing the pedicle screw.

The invention claimed is:

1. A method for recovering a positioned locator-pin (110-210) from a patient, wherein the locator-pin (110-210) comprises a smooth pin body (112), a distal portion comprising a smooth trocar tip (114) shaped to penetrate a bone by pressing and/or percussing, and a proximal portion (116) equipped with a first fixing member (118) to fix, during use, to an insertion pin-carrier (120) equipped with a fixing member (121) complementary to the first fixing member (118) of the locator-pin and a second fixing member (119) to fix, during use, to a removal pin-carrier (130), the two fixing members (118, 119) being different, wherein the first fixing member (118) is able to transmit at least an axial push parallel to an axis of a locator-pin, and the second fixing member (119) is able to transmit at least an axial draw parallel to the axis of the locator-pin and at least one sense of rotation around the axis of the locator-pin, the method comprising:

providing a removal pin-carrier (130) equipped with a fixing member (131) complementary to the second fixing member (119) of the locator-pin, making an incision to disengage a proximal portion (116, 216) of the positioned locator-pin, providing a guide cannula (140) designed to receive freely sliding the locator-pin (110), the insertion pin-carrier (120) and the removal pin-carrier (130), and reinserting the guide cannula (140), encasing the locator-pin and following its path into the pedicle of vertebra O, introducing the removal pin-carrier (130) into the guide cannula (140) and screwing onto a threaded portion (119) of the locator-pin (110) to secure the locator-pin and removing the locator-pin through the guide cannula (140), which is left in place.

2. The method of claim 1, wherein the first fixing member of the locator pin is a bayonet fixing member and the second fixing member is a threaded fixing member.

3. The method of claim 2, wherein the bayonet fixing member of the locator pin comprises a lug (118) arranged radially on the proximal portion (116) of the locator-pin, and designed to slide axially, during use, in a groove (121) located in the insertion pin-carrier (120); and the threaded fixing member is a threaded portion (119) arranged on the proximal portion (116) of the locator-pin, between the first fixing member (118) and a proximal end of the locator-pin, and designed to be screwed, during use, into a tapped hole (131) located in the removal pin-carrier (130).

4. The method of claim 2, wherein the bayonet fixing member of the locator pin comprises a groove (218) arranged on the proximal portion (216) of the pin, and designed to receive, during use, a lug (222) arranged radially in a cavity (224) located in the insertion pin-carrier (220) and the threaded fixing member is a threaded portion (119) arranged on the proximal portion (216), between the first fixing member (218) and a proximal end of the locator-pin, and designed to be screwed, during use, into a tapped hole (131) located in the removal pin-carrier (130).

5. The method of claim 2, wherein a flat surface (115) is provided between the proximal portion (116) and the pin body (112) of the locator pin.

6. The method of claim 1, wherein the insertion pin-carrier (120) of the locator-pin comprises a cylindrical body, a proximal end equipped with a gripping handle (126), a distal end (124) equipped with a groove (121) designed to receive, during use, a lug (118) located in the locator-pin (110), the groove (121) being arranged to enable radial locking of the lug (118) and a tubular cavity (122) designed to receive sliding freely, during use, a threaded portion (119) located on the locator-pin.

7. The method of claim 1, wherein the insertion pin-carrier (120) of the locator-pin comprises a cylindrical body (226), a proximal end equipped with a gripping handle (228), a distal end equipped with a tubular cavity (224) designed to receive sliding freely, during use, a threaded portion (119) located on the locator-pin (210) and a lug (222) arranged radially in the tubular cavity (224) and designed to engage, during use, in a groove (218) arranged on a proximal portion (216) of the locator-pin (210) to enable radial locking of the lug (222).

8. The method of claim 1, wherein the removal pin-carrier of a locator-pin (110-210) comprises a cylindrical body (132), a proximal end equipped with a gripping handle (133) and a distal end equipped with a tapped hole (131) designed to be screwed, during use, onto a threaded portion (119) located on a locator-pin (110-210).

* * * * *